(12) United States Patent
Cumming (10) Patent No.: US 7,553,327 B2
(45) Date of Patent: Jun. 30, 2009

(54) ACCOMMODATING 360 DEGREE SHARP EDGE OPTIC PLATE HAPTIC LENS

(75) Inventor: J. Stuart Cumming, Laguna Beach, CA (US)

(73) Assignee: The Nice Trust, A Trust Of The Isle of Man (IM)

( * ) Notice: Subject to any disclaimer, the term of this patent is extended or adjusted under 35 U.S.C. 154(b) by 511 days.

(21) Appl. No.: 10/888,163

(22) Filed: Jul. 8, 2004

(65) Prior Publication Data

US 2005/0125057 A1    Jun. 9, 2005

Related U.S. Application Data (60) Provisional application No. 60/527,340, filed on Dec. 4, 2003.

(51) Int. Cl.
*A61F 2/16* (2006.01)

(52) U.S. Cl. ............... 623/6.37; 623/6.16; 623/6.44

(58) Field of Classification Search ............ 623/6.11, 623/6.16, 6.17, 6.37, 6.38–6.54
See application file for complete search history.

(56) References Cited

U.S. PATENT DOCUMENTS

| | | | |
|---|---|---|---|
| 4,174,543 A | 11/1979 | Kelman |
| 4,244,060 A | 1/1981 | Hoffer |
| 4,254,509 A | 3/1981 | Tennant |
| 4,254,510 A | 3/1981 | Tennant |
| 4,298,996 A | 11/1981 | Barnet |
| 4,304,012 A | 12/1981 | Richard |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,664,666 A | 5/1987 | Barrett |
| 4,673,406 A | 6/1987 | Schlegel |
| 4,704,123 A | 11/1987 | Smith |
| 4,718,904 A | 1/1988 | Thornton |

(Continued)

FOREIGN PATENT DOCUMENTS

EP    0336877 A1    10/1989

(Continued)

OTHER PUBLICATIONS

Lee, Judith, "Update on IOLs," Outpatient Surgery (Mar. 2002), printed Oct. 26, 2004 (http://www.outpatientsurgery.net/2002/os03/f4.shtml).

(Continued)

*Primary Examiner*—William H. Matthews
(74) *Attorney, Agent, or Firm*—Orrick Herrington & Sutcliffe LLP (57) ABSTRACT

An accommodating intraocular lens having an optic and portions extending from the optic radially outwards preferably with fixation devices at their distal ends, the optic designed such that it has a sharp posterior edge for 360 degrees of its perimeter and the lens designed such that the optic can move forward and backwards with constriction and relaxation of the ciliary muscle.

19 Claims, 7 Drawing Sheets

U.S. PATENT DOCUMENTS

| | | |
|---|---|---|
| 4,738,680 A | 4/1988 | Herman |
| 4,753,655 A | 6/1988 | Hecht |
| 4,759,761 A | 7/1988 | Portnoy |
| 4,778,463 A | 10/1988 | Hetland |
| 4,813,955 A | 3/1989 | Achatz et al. |
| 4,840,627 A | 6/1989 | Blumenthal |
| 4,842,601 A | 6/1989 | Smith |
| 4,880,427 A | 11/1989 | Anis |
| 4,936,850 A | 6/1990 | Barrett |
| 4,963,148 A | 10/1990 | Sulc et al. |
| 4,994,082 A | 2/1991 | Richards et al. |
| 5,047,051 A | 9/1991 | Cumming |
| 5,078,742 A | 1/1992 | Dahan |
| 5,171,319 A | 12/1992 | Keates et al. |
| 5,217,490 A | 6/1993 | Sayano et al. |
| 5,376,115 A | 12/1994 | Jansen |
| 5,476,514 A | 12/1995 | Cumming |
| 5,496,366 A | 3/1996 | Cumming |
| 5,522,891 A | 6/1996 | Klaas |
| 5,674,282 A | 10/1997 | Cumming |
| 6,197,059 B1 | 3/2001 | Cumming |
| 6,387,126 B1 | 5/2002 | Cumming |
| 6,494,911 B2 | 12/2002 | Cumming |
| 6,558,419 B1 | 5/2003 | Pham et al. |
| 6,638,306 B2 | 10/2003 | Cumming |
| 2001/0001836 A1 | 5/2001 | Cumming |
| 2002/0138140 A1* | 9/2002 | Hanna ............... 623/6.37 |
| 2003/0158599 A1* | 8/2003 | Brady et al. ............... 623/6.37 |
| 2004/0002757 A1 | 1/2004 | Lai et al. |
| 2005/0021140 A1* | 1/2005 | Liao ............... 623/6.37 |

FOREIGN PATENT DOCUMENTS

| | | |
|---|---|---|
| FR | 1103399 | 11/1955 |
| GB | 2171912 A | 9/1986 |

OTHER PUBLICATIONS

Zhang, Z. et al., "A clinical study of posterior capsular opacification after implantation of foldable intraocular lenses with different edges of optics," Zhonghua Yan Ke Za Zhi 38(10):606-609 (Oct. 2002), printed Oct. 26, 2004 (http://www.ncbi.nlm.nih.gov/entrez/query.fcgi?cmd=Retrieve&db=pubmed&dopt=Abstract&list...).

Masket, Samuel, "Continuing Medical Education: Oct. 2003 IOL Edge Design, and PCO Dysphotopsia," Review of Ophthalmology, printed Oct. 26, 2004 (http://www.revophth.com/index.asp?ArticleType=SiteSpec&page=cme/oct03/lesson.htm).

Sabbagh, Leslie, "IOL Design Closes OffPCO," Review of Ophthalmology, printed Oct. 26, 2004 (http://www.revophth.com/index.asp?page=1_255.htm).

Disclosure Document Deposit Request dated Sep. 30, 2003, PTO Disclosure Document No. 539449.

Archimede Busacca, Ciliary Muscle Physiology Studied by Gonioscopy, Annals of Oculistics, vol. CLXXXVIII, Jan. 1955 (English Translation).

Archimede Busacca, La Physiologid Du Muscle Ciliarire Etudiee par la Gonioscopie, Annales D'Oculistique, vol. CLXXXVIII, 1st Livraison, Janvier 1955 (French Translation).

D. Jackson Coleman, M.D., On the Hydraulic Suspension Theory of Accommodation, Tr. Am. Opth. Soc. vol. LXXXIV, pp. 846-868, 1986.

J. Stuart Cumming, M.D., Accommodating Intra-Ocular Lens Development & Clinical Results, PowerPoint presentation 1999-2000.

Spencer Thornton, "Accommodating in Pseudophakia," Color Atlas of Lens Implantation, Chapter 25, pp. 159-161.

* cited by examiner

ACCOMMODATING 360 DEGREE SHARP EDGE OPTIC PLATE HAPTIC LENS

The present application is a regular utility application claiming priority from U.S. provisional patent application Ser. No. 60/527,340 filed Dec. 4, 2003, applications Ser. No. 10/454,280, filed Jun. 3, 2003, now U.S. Pat. No. 7,048,760, which is a continuation of Ser. No. 10/057,691, filed on Jan. 24, 2002, now U.S. Pat. No. 6,638,306, which is a division of application Ser. No. 08/858,978, filed on May 20, 1997, now U.S. Pat. No. 6,387,126, which is a continuation-in-part of application Ser. No. 08/388,735, filed on Feb. 5, 1995, now abandoned, the disclosures of which are all incorporated by this reference.

BACKGROUND

Intraocular lenses have for many years had a design of a single optic with loops attached to the optic to center the lens and fixate it in the empty capsular bag of the human eye. In the mid '80s silicone plate lenses were introduced, which were 10.5 mm in length and had a 6 mm optic. These lenses did not fixate well in the capsular bag, but resided in pockets between the fused anterior and posterior capsules. The first foldable lenses were all made of silicone.

In the mid 1990s an acrylic material was introduced as the optic of lenses. The acrylic lens had a biconvex optic with a straight edge into which was inserted loops to center the lens in the eye and fixate it within the capsular bag. Claims were made that the material of this lens significantly reduced posterior capsular opacification. It later became apparent that the property of the lens that reduced posterior capsular opacification was not necessarily related to the material, but to the relatively sharp or "square edge" on the posterior surface of the optic. The optic, when it is sealed within the capsular bag, presented a square sharp edge to the posterior capsule, which is tightly pulled against it during the period of fibrosis, preventing the ectodermal cells from growing across the posterior capsule behind the optic. A barrier was formed which successfully reduced the posterior capsular opacification rate. Silicone optic lenses were manufactured with a similar so-called straight edge in the posterior surface of the optic. Studies were done and the instance of posterior capsular opacification was found to be the same in the silicone lenses as in the acrylic lenses; therefore the material was not the cause of the reduction of the reduction in posterior capsular opacification. The sharp edge of the optic where the posterior optic surface joined the edge of the lens was the prime reason for the reduced incidence of posterior capsule opacification.

Recently accommodating intraocular lenses have been introduced to the market, which are modified plate haptic lenses and, like the standard silicone plate haptic lenses, have no clear demarcation between the junction of the plate with the optic's posterior surface. A plate haptic lens may be defined as an intraocular lens having two or more plate haptics where combined junctions with the optic represent one quarter or more of the circumference of the optic.

SUMMARY OF THE INVENTION

The objective of this invention is to provide an optic in a plate lens design with a 360 degree sharp edge.

DESCRIPTION OF THE PREFERRED EMBODIMENTS

Figure 5A:
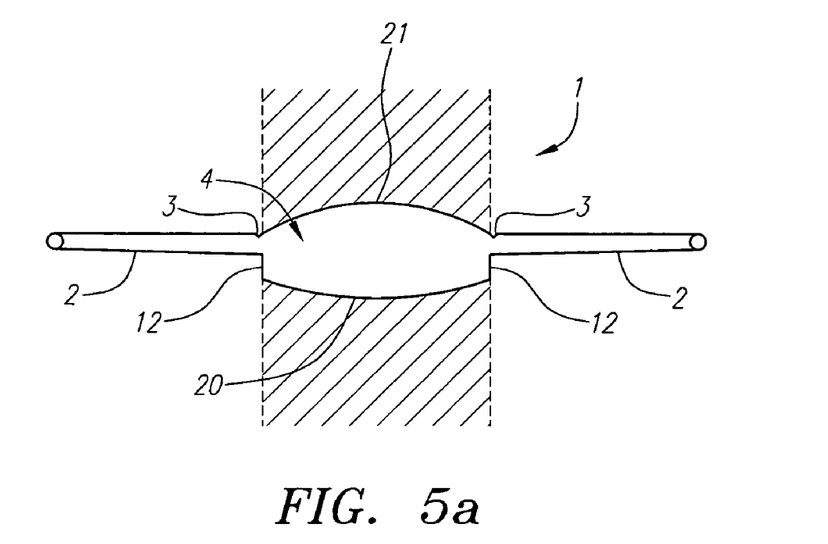
FIG. 5a diagrammatically illustrates how the sharp 360 degree edge is formed.
Figure 5B:
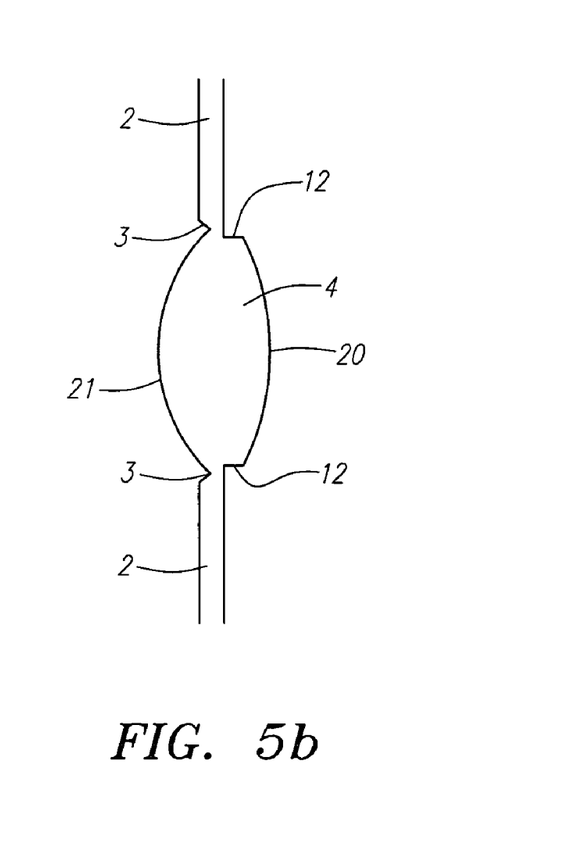
FIG. 5b shows a side view of the preferred posterior optic surface of all the lenses shown in Figures.
Figure 9:
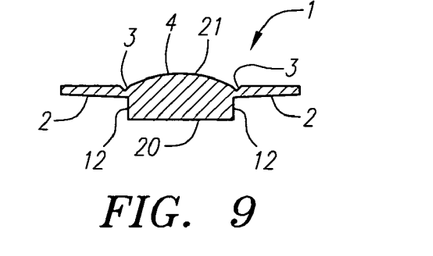
FIG. 9 is a cross section of the lens of FIG. 8 showing the 360 degree sharp edge on the posterior surface of the optic.
Figure 11:
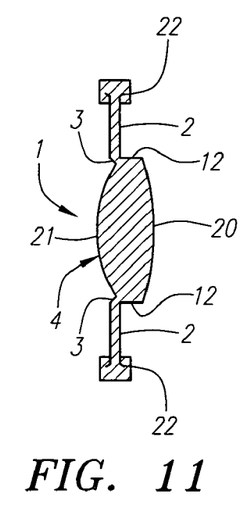
FIG. 11 is a cross section of the lens of FIG. 10 showing the sharp 360 degree edge on the posterior surface of the optic.

The purpose of the invention is to provide a sharp edge for 360 degrees on the posterior surface of the optic of a haptic, probably a plate-haptic, intraocular lens. Standard plate or other lenses can have a sharp edge through the section of the periphery of the optic that is not adjacent to the plate. The essence of this invention is that the lens optic has a sharp edge for 360 degrees, thus preventing or reducing the opacification of the posterior capsule after implantation of the lens into the capsular bag of the human eye. The cross section of the lens in FIGS. 5b, 9 and 11 shows flexible plate haptics 2 adjacent to an optic 4, and shows hinges 3 formed by grooves across the haptics on the anterior side. The anterior surface 21 of the optic 4 opposes the posterior surface 20. The sharp edge 12 is clearly shown on the posterior surface and extends for 360 degrees. The lens is an accommodating lens such that the optic is moveable anteriorly and posteriorly relative to the outer ends of the haptics, the lens being designed to produce a maximal movement of the optic relative to the outer ends of the plates. FIG. 5a diagrammatically shows how the 360 degree edge is formed.

The lens comprises extending portions which may be plates with either integrally formed loops of the same material as the extended portions or with T-shaped loops of a different material, such as polyimide, prolene, or PMMA. The loops are flexible such that the tip-to-tip diameter may be 11 to 13 mm outside the radius of the capsular bag, but the loops flex down toward the optic when placed in the capsular bag, thereby ensuring excellent centration of the optic and fixation of the lens. The loops may be sized to be independent of contact or be in contact with the ciliary muscle through the capsular bag wall.

Figure 6:
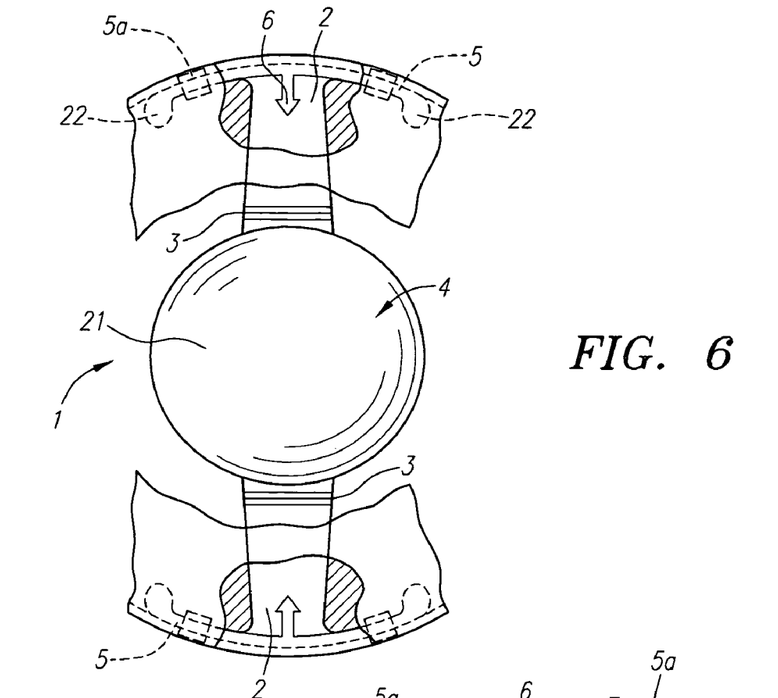
FIG. 6 is a T-shaped variation of an accommodating lens demonstrating the flexibility of the loops, which is also shown in FIG. 7.
Figure 7:
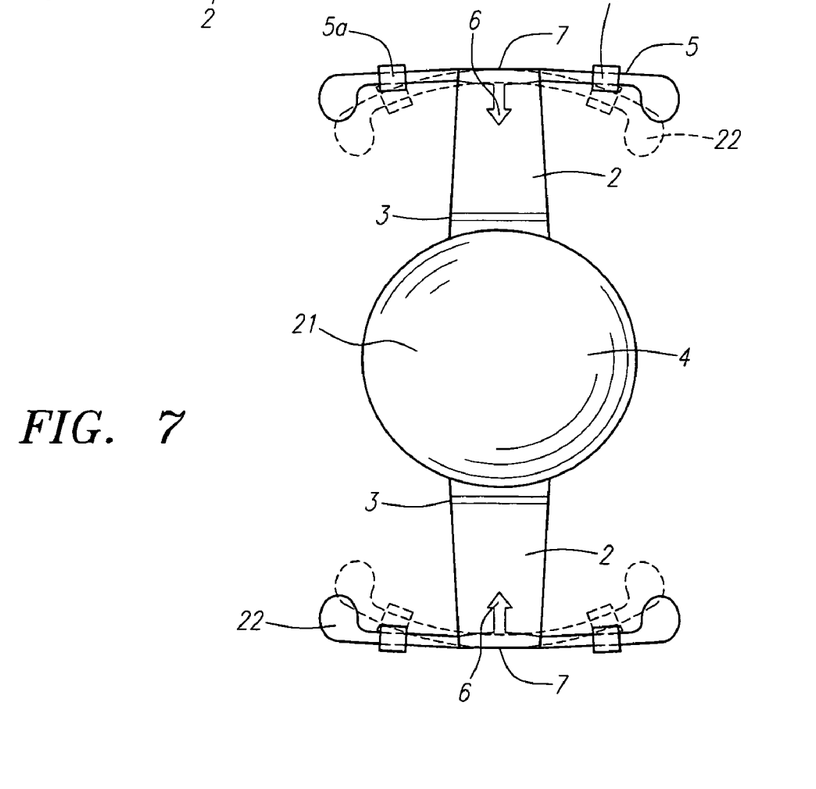
FIG. 7 shows the flexibility of the loops relative to the optic of the lens of FIG. 6.

Referring to FIGS. 6 and 7 of the drawings, a preferred form of the intraocular lens 1 is shown wherein the lens comprises two components, namely a flexible optic 4 and plate haptics 2 which are capable of multiple flexions without damage. These two Figures show a plate haptic design with T-shaped flexible loops 5 extending from the corners of each of the plates 2. Collars 5a also can be provided if desired at the outer ends of the loops 5. Hinges 3 facilitate the anterior and posterior movement of the optic relative to the outer ends of the plates. Internal elastic strain can cause the lens to move anteriorly and posterior capsule elasticity can cause the lens to move anteriorly. One or more plate haptics 2 extend distally from opposite sides of the optic. The haptics are plate haptics, preferably having arcuate outer edges. Loops 5 when unrestrained, are somewhat less curved in configuration than shown in FIG. 6. The loops 5 provide laterally extending flexible fixation fingers. The lens, including the optic 4, haptics 2, and loops 5 is preferably formed of flexible material such as silicone, acrylic, or hydrogel, preferably of a material that does not fracture with time. The fixation devices may be of a different material than the plate, such as polyimide, prolene, or PMMA and are molded into the distal ends of the plate as is described later with reference to FIGS. 2 through 4.

Figure 1A:
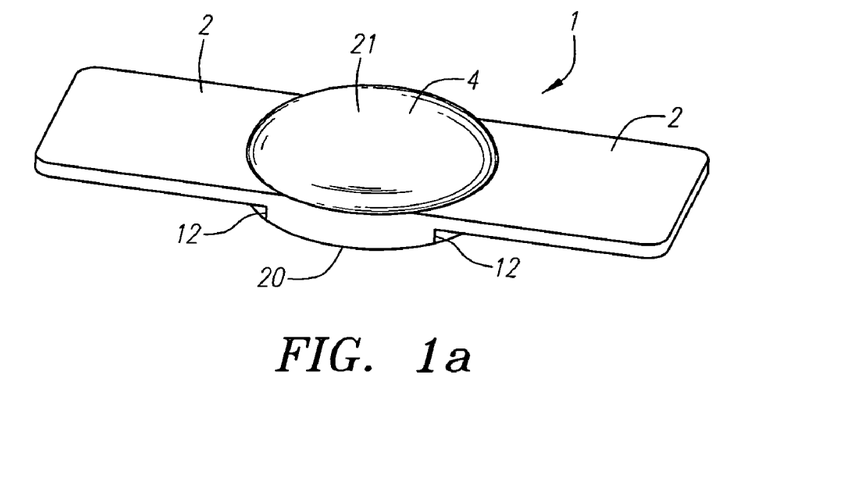
FIG. 1a is a perspective view of a simple plate lens without hinges, illustrating the sharp edge on the posterior surface of the optic.
Figure 1B:
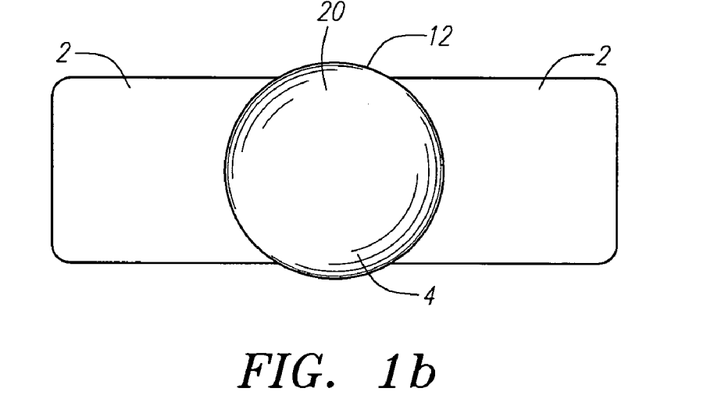
FIG. 1b is a plan view of the lens of FIG. 1a, looking at it from the posterior surface with the sharp edge surrounding the optic.
Figure 2:
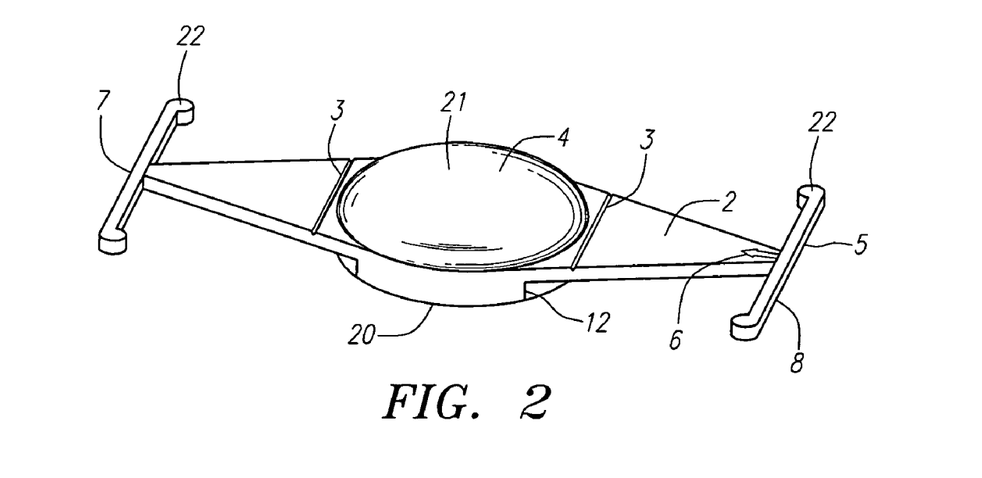
FIG. 2 shows a similar lens with T-shaped haptics and hinges across the plates adjacent to the optic.
Figure 3:
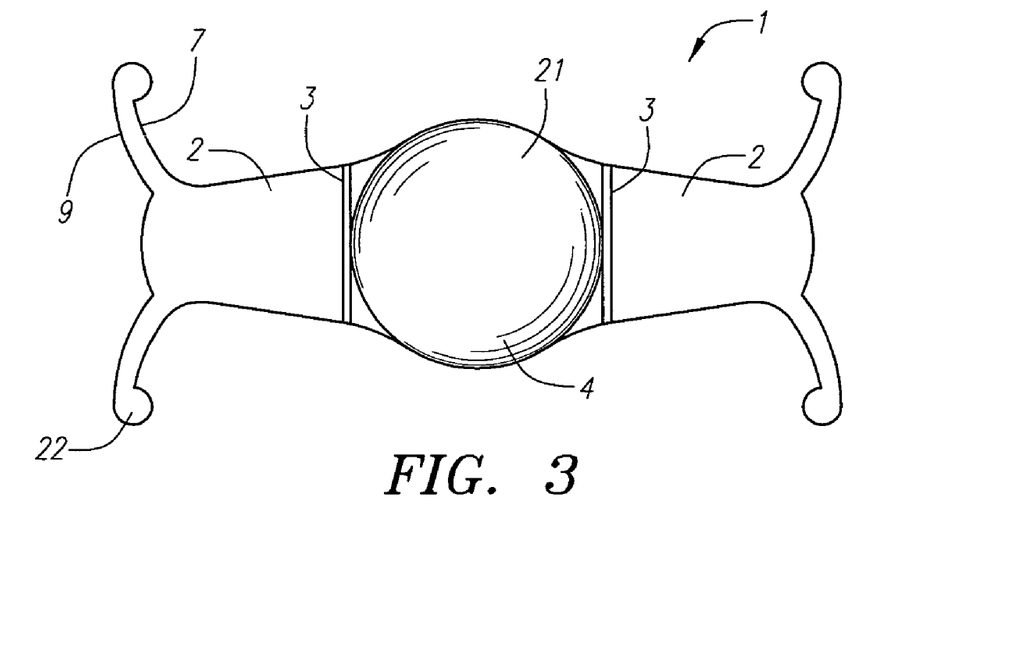
FIG. 3 shows a T-shaped lens where T projections are made of flexible material, such as the plate, with fixation devices at the terminations.
Figure 4:
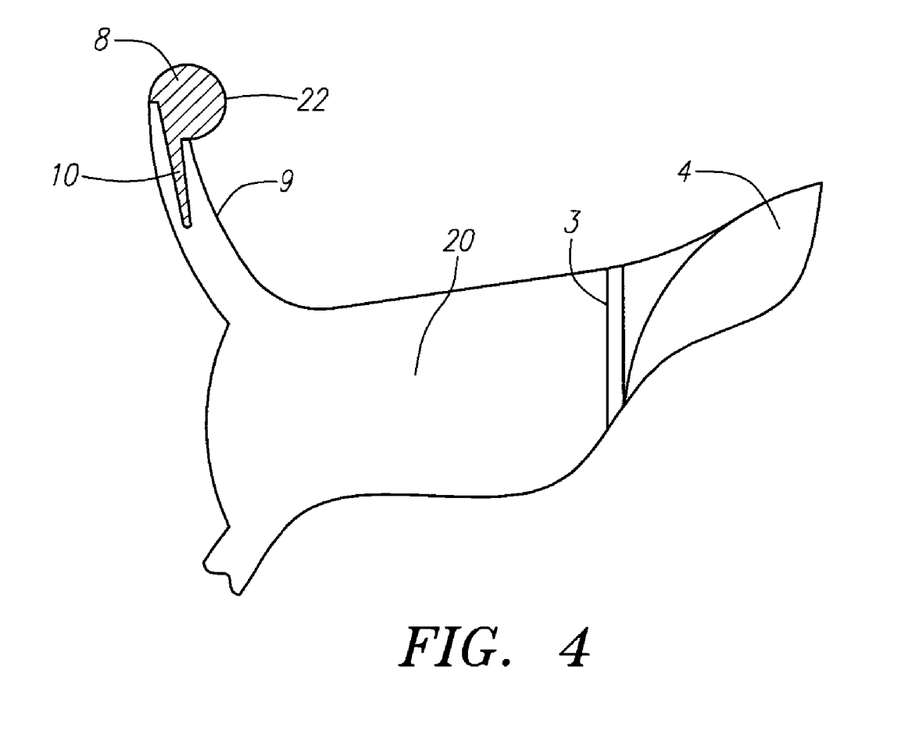
FIG. 4 shows detail of the fixation device.

As is well known in the art, an intraocular lens such as that of the various Figures is implanted in the capsular bag of the eye after removal of the natural lens. The lens is inserted into the capsular bag by a generally circular opening cut in the anterior capsular bag of the human lens and through a small opening on the cornea or sclera. The outer ends of the haptics, having loops on their distal edges, are positioned in the cul-de-sac of the bag. The loops 5 are in close proximity with the bag cul-de-sac, the loops being deflected from the configuration shown centrally toward the optic as seen in FIG. 6 and shown in dashed lines in FIG. 7. The loops are shown in their central position in FIG. 7. Knobs 22 can be provided on the outer end portions of the loops (note, e.g., FIGS. 2 through 4, 6, 10 through 12, and 15 through 17) for improved securement in the capsular bag or cul-de-sac by engagement with fibrosis which develops in the capsular bag following the surgical removal of the central portion of the anterior capsular bag. The end of the loops containing the knobs may be either integrally formed from the same material as the plates or may be of separate material such as polyimide, prolene, or PMMA 5, as shown in FIGS. 2 through 4. The loop 7 in FIG. 2 is integrally formed with the plate 2, whereas loop 8 is of a separate material and is secured to the haptic 2 at 6. The junction in FIG. 2 of the posterior surface of the optic 4 to the edge of the lens is a sharp junction 12 designed to reduce the migration of cells across the posterior capsule of the lens postoperatively and thereby reduce the incidence of posterior capsular opacification and the necessity of YAG posterior capsulotomy. The anterior surface of the lens 21 is closer to the groove or hinge 3 than the posterior surface 20.

The loops 8 formed of a separate material in FIG. 4 are molded into the terminal portions of the plates 2 such that the flexible material of the loop can extend by elasticity along the internal fixation member 10 of the loop 8. The plates 2 may have a groove or hinge 3 across its surface adjacent to the optic. This facilitates the anterior and posterior movement of the optic relative to the outer ends of the haptics. A hard knob 22 on the end of the loops 7 or 8 is designed to fixate the loops in the capsular bag and at the same time allow the elastic loop to stretch along its length as the optic of the lens moves backwards and forwards and the plate haptics move or slide within a pocket formed between the fusion of the anterior and posterior capsules of the capsular bag. Internal elastic strain can cause the lens to move anteriorly and posterior capsule elasticity can cause the lens to move anteriorly.

Figure 8:
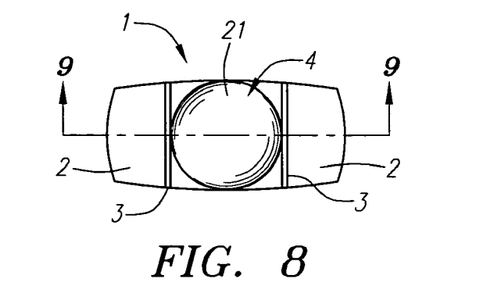
FIG. 8 is an elevational view of a lens having a flexible optic and flexible plate haptics extending oppositely from the optic, the plate haptics having grooves or hinges across their plates adjacent to the optic.
Figure 10:
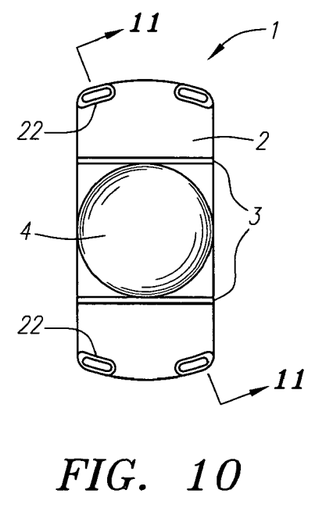
FIG. 10 is another version of the lens with the fixation devices being on the end of the plates comprising projections on the anterior, posterior, or both surfaces at the distal ends of the plates.
Figure 12:
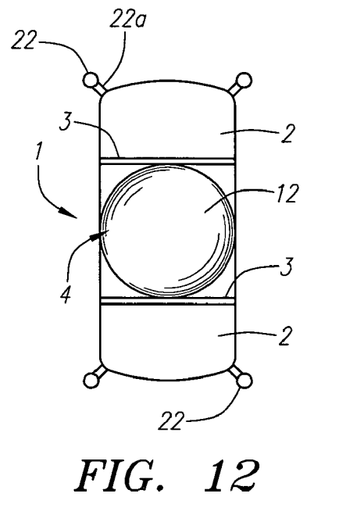
FIG. 12 is another version with different fixation devices extending from the corners of each of the plates.
Figure 13:
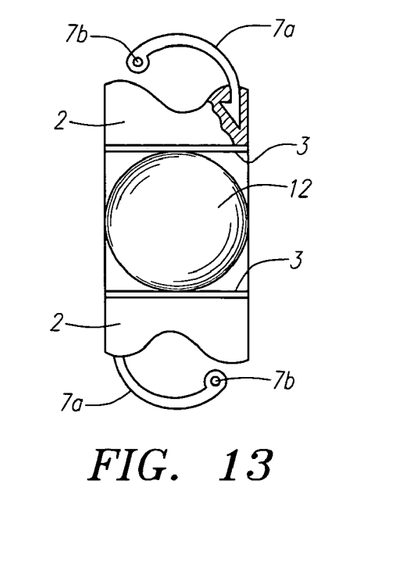
FIG. 13 is an elevational view of yet another version of the accommodating lens with plates fixated to the optic and flexible loops of a different material extending from the ends of the plates.
Figure 14:
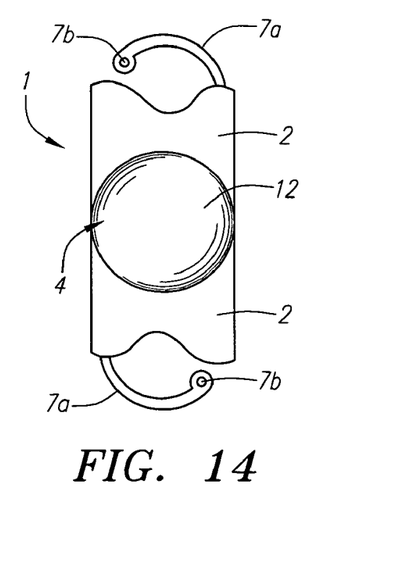
FIG. 14 is similar to FIG. 13 except that there are no hinges across the plates as shown in FIG. 13, the haptics being sufficiently resilient such that they do not require hinges.

Turning to other embodiments, FIG. 8 shows a simple plate lens design with hinges 3 across the plates. FIG. 10 shows a plate lens with one or more fixation devices 22 on the distal ends of the plates projecting from either the anterior or posterior or both sides of the plates. FIGS. 9 and 11 show a cross section of the respective lenses of FIGS. 8 and 10. Raised fixation members in the form of knobs 22 can be provided on the outer end portions of the loops. FIG. 12 shows another lens where the fixation devices are knobs 22 on the ends of small protrusions 22a at the corners of each of the plate haptics. FIG. 13 shows another accommodating lens whereby the fixation and centration device is formed of loops 7a that are molded into the plate haptic. Holes 7b also can be provided in the ends of the loops. In FIG. 14 there is no groove across the plate, the plate being sufficiently flexible that a hinge mechanism is not required.

Figure 15:
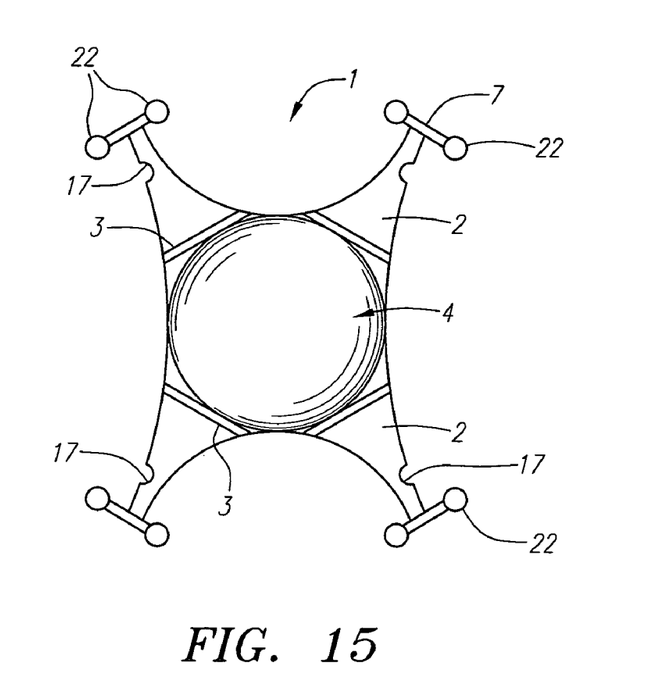
FIG. 15 shows a lens with multiple plate haptics and T-shaped fixation devices at the peripheral ends.
Figure 16:
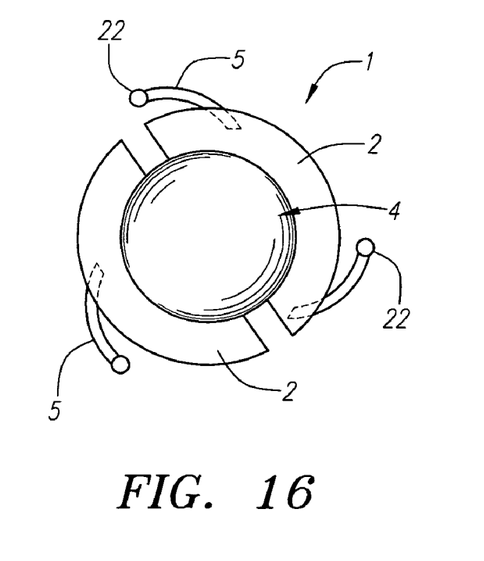
FIG. 16 is another variation of a hybrid lens with two half-discs and fixation devices at their periphery.
Figure 17:
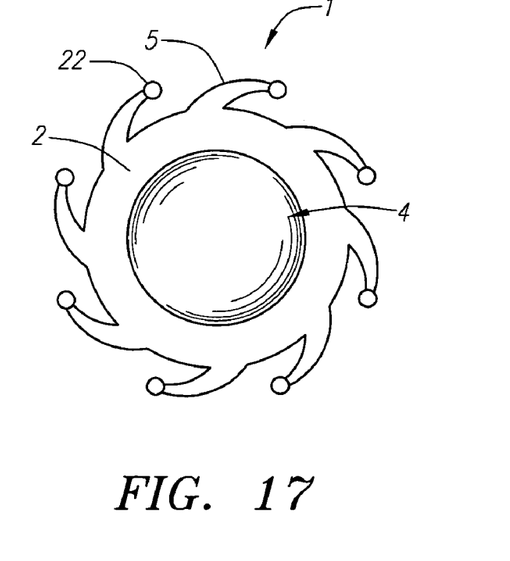
FIG. 17 is a complete disc surrounding the optic with fixation and centration devices attached to the rim of the disc.

FIG. 15 shows another variation of the lens with four plates and four hinges, and a T-section at the end of each plate with knobs 22 on the ends for fixation in the eye. There also can be notches 17 in the plates to further enhance the fixation of the distal part of the plate into the eye. FIG. 16 shows a disc variation of a lens with two half plates with loops 5 and a knob 22 at the end for fixation and centration of the lens within the eye. FIG. 17 shows another variation of the circular plate design with one or more centration and fixation devices about the periphery of the flexible plate with a central optic. In FIGS. 10-12 and 15-17, the knobs are laterally extended.

Figure 18:
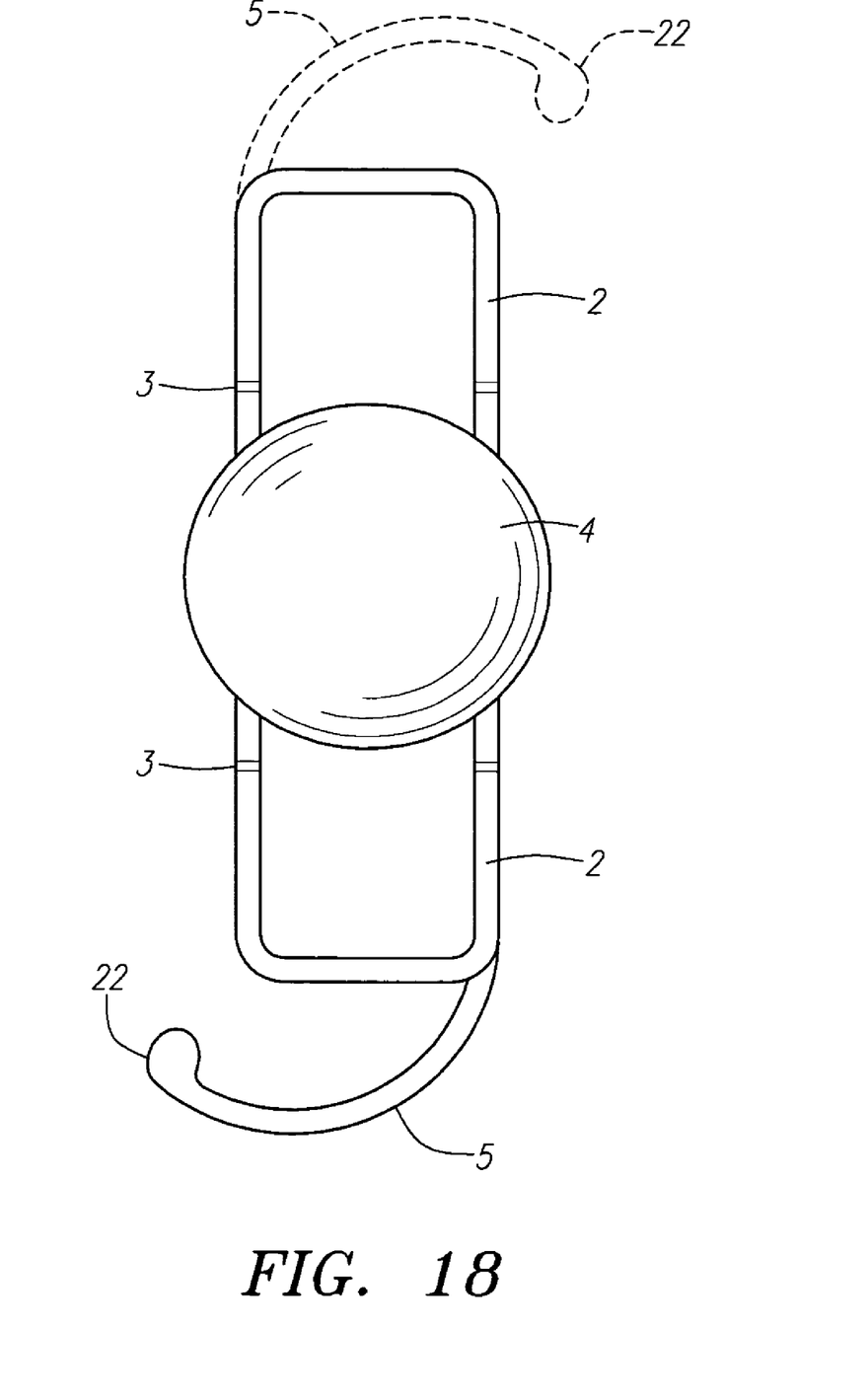
FIG. 18 shows an alternative embodiment.

FIG. 18 illustrates an alternative embodiment wherein the extending portions or haptics are in the form of thin members 2, extending from the optic 4. Centration/fixation loops 5 can be added to both outer ends or not added as desired, and likewise hinges 3 as shown can be provided on both sets of haptics or omitted from both as desired. Furthermore, knobs 22 can be provided at the ends of loops 5, or omitted.

Many changes, modifications, variations, and other uses and applications of the subject invention will, however, become apparent to those skilled in the art after considering this specification together with the accompanying drawings and claims. All such changes, modifications, variations, and other uses of the applications which do not depart from the spirit and scope of the invention are deemed to be covered by the invention, which is limited only by the claims which follow.

What is claimed is:

1. An accommodating intraocular lens wherein the lens comprises a uniformly flexible uniplanar lens body having normally anterior and posterior sides, including a flexible optic, said lens body having two or more straight uniformly flat oblong plate like radially extending flexible portions each having one groove or hinge across the extending portions and adjacent the optic and which include laterally extending flexible fixation fingers at their outer ends which are made of material different from that of the extending portions such that the lens can move anteriorly with contraction of the ciliary muscle of the eye, the radially extending portions comprise flat plate haptics with thin narrow straight lateral edges and wider anterior and posterior surfaces than the narrow lateral edges and the groove or hinge is across the wider surface, the optic having a sharp edge for 360 degrees on the posterior side of the optic, and the lens being sized to be implanted into the capsular bag of the eye such that contraction of the ciliary muscle causes the lens within the capsular bag behind the iris to move forward towards the iris with its contraction.

2. An accommodating lens according to claim 1 wherein the lens is sized such that it is not to be in contact with the ciliary muscle through the capsular bag wall.

3. An accommodating lens according to claim 1 wherein the lens can move anteriorly and posteriorly.

4. An accommodating lens according to claim 1, wherein the outer ends of the extending portions can move anteriorly and posteriorly relative to the optic.

5. An accommodating lens according to claim 1, wherein internal elastic strain causes the lens to move anteriorly.

6. An accommodating lens according to claim 1, wherein posterior capsule elasticity can cause the lens to move anteriorly.

7. An accommodating lens according to claim 1, wherein the optic can move forward and backwards with ciliary muscle contraction and relaxation.

8. An accommodating lens according to claim 1, in which the optic and extending portions are made from different materials.

9. An accommodating lens according to claim 1, wherein the extended portions are plate haptics and have hinges.

10. An accommodating lens according to claim 9, wherein the plate haptics have a widening of the plate junctions adjacent to the optic.

11. An accommodating lens according to claim 1, wherein constriction of the ciliary muscle can produce forward movement of the lens optic within the capsular bag towards the iris for near vision.

12. An accommodating lens according to claim 1, wherein the plate haptics have raised fixation members at their outer ends on either or both surfaces.

13. An accommodating lens according to claim 1, wherein the one of a groove or hinge across the plate haptic adjacent to the optic is on the anterior side thereof.

14. An accommodating lens according to claim 1, wherein the extending portions have distal ends with corners, the corners having knobs.

15. An accommodating lens according to claim 1, wherein the extending portions include hinged plate haptics with laterally extending flexible fingers.

16. An accommodating lens according to claim 1, wherein the optic is located posteriorly to the outer ends of the extending portions.

17. An accommodating lens according to claim 1, wherein the extending portions comprise plates flexible throughout their length whereby the optic is anterior to the outer ends of the plates.

18. An accommodating lens according to claim 1, wherein the optic is biconvex.

19. An accommodating lens according to claim 1, wherein the optic has a relatively flat front surface and a posterior surface with a smaller radius of curvature.

* * * * *

UNITED STATES PATENT AND TRADEMARK OFFICE
CERTIFICATE OF CORRECTION

PATENT NO. : 7,553,327 B2 Page 1 of 1
APPLICATION NO. : 10/888163
DATED : June 30, 2009
INVENTOR(S) : J. Stuart Cumming

It is certified that error appears in the above-identified patent and that said Letters Patent is hereby corrected as shown below:

Title page, item (73) should read as follows:

(73) Assignee: C & C Vision International Limited

Signed and Sealed this

Sixteenth Day of March, 2010

David J. Kappos
*Director of the United States Patent and Trademark Office*